US006225518B1

(12) United States Patent
Sohn et al.

(10) Patent No.: US 6,225,518 B1
(45) Date of Patent: May 1, 2001

(54) OLEFINIC HYDROCARBON SEPARATION PROCESS

(75) Inventors: Stephen Wayne Sohn, Arlington Heights; Santi Kulprathipanja, Inverness, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/407,166

(22) Filed: Sep. 28, 1999

Related U.S. Application Data
(60) Provisional application No. 60/101,974, filed on Sep. 28, 1998.

(51) Int. Cl.[7] .............................. C07C 7/13; C10G 25/03
(52) U.S. Cl. .................... 585/826; 585/802; 585/809; 585/820; 585/822; 585/827; 585/829; 208/310 Z
(58) Field of Search .............................................. 585/826

(56) References Cited

U.S. PATENT DOCUMENTS

| 3,878,128 | * | 4/1975 | Rosback | 252/455 Z |
| 3,888,939 | * | 6/1975 | Rosback | 260/677 AD |
| 3,929,669 | * | 12/1975 | Rosback et al. | 252/455 Z |
| 4,473,657 | * | 9/1984 | Tse et al. | 502/37 |
| 5,276,246 | | 1/1994 | McCulloch et al. | 585/829 |
| 5,292,990 | | 3/1994 | Kantner et al. | 585/820 |
| 5,300,715 | | 4/1994 | Vora | 585/254 |
| 6,106,702 | * | 8/2000 | Sohn et al. | 208/310 Z |

OTHER PUBLICATIONS

"Olex: A Process for Producing High Purity Olefins," by J.A. Johnson, S. Raghuram and P.R. Pujado, presented at the American Institute of Chemical Engineers, Aug. 16–19, 1987.

* cited by examiner

Primary Examiner—Ellen M. McAvoy
(74) Attorney, Agent, or Firm—John G. Tolomei; John F. Spears, Jr.

(57) ABSTRACT

A molecular sieve used in a process for separating olefinic hydrocarbons from paraffinic hydrocarbons is regenerated in a method which removes diolefins and aromatic hydrocarbons from the molecular sieve. The method comprises contacting the sieve with alkaline water and then drying the sieve with stream of a superheated light paraffin. The molecular sieve may be present in either a guard bed used upstream of a main separation zone or as part of the main adsorptive separation zone.

15 Claims, No Drawings

US 6,225,518 B1

OLEFINIC HYDROCARBON SEPARATION PROCESS

This application claims the benefit of the filing date of Provisional Application No. 60/101,974 filed Sep. 28, 1998.

FIELD OF THE INVENTION

The invention relates to a process for the adsorptive separation of hydrocarbons from a feed mixture comprising the hydrocarbons and a different type of hydrocarbons such as the separation of olefins from paraffins. The invention more specifically relates to a method for the regeneration of a molecular sieve used either as a guard bed or as the main adsorbent in such a process.

RELATED ART

Molecular sieves are widely used to separate different structural types of hydrocarbons. For instance, it is known in the art that adsorptive separation using a molecular sieve adsorbent is an effective method to separate linear olefinic hydrocarbons from a feed mixture comprising the olefinic hydrocarbons and another class of hydrocarbons having a similar volatility such as paraffins of the same general molecular weight. This process is described in a paper entitled Olex: *A Process for Producing High Purity Olefins* presented by J. A. Johnson, S. Raghuram and P. R. Pujado at the August 1987 Summer national meeting of the American Institute of Chemical Engineers in Minneapolis, Minn. This paper describes a simulated moving bed (SMB) countercurrent adsorptive separation process for the separation of light straight chain olefins from similar paraffins.

U.S. Pat. No. 5,276,246 issued to B. McCulloch et al. describes a process for the adsorptive separation of normal olefins from a mixture of normal olefins and branched chain olefins using a low acidity silica molecular sieve such as a silicalite or ZSM molecular sieve.

U.S. Pat. No. 5,292,990 issued to E. Kantner et al. describes an adsorptive separation process for the recovery of linear olefins or paraffins from a mixture which also contains branched aliphatic hydrocarbons. The process employs an adsorbent comprising a low acidity high silica to alumina ratio zeolite. U.S. Pat. No. 5,300,715 issued to B. V. Vora describes an overall process for the conversion of paraffins to olefins. The process includes dehydrogenation of the paraffins and adsorptive separation of the olefins from a paraffin/olefin mixture recovered from the effluent of the dehydrogenation zone. The patent describes a zone used to selectively remove aromatic hydrocarbons from the paraffin/olefin mixture to prevent the aromatic hydrocarbons from deactivating a molecular sieve used in an adsorptive separation of the paraffin/olefin mixture. The removal of the aromatics also aids the performance of the dehydrogenation zone of the process. The aromatics removal zone is taught as possibly containing a molecular sieve, which is regenerated as needed.

BRIEF SUMMARY OF THE INVENTION

The invention is a process for the adsorptive separation of olefinic hydrocarbons from other hydrocarbons characterized in that a molecular sieve used in the process is regenerated in a novel multistep procedure which comprises purging the feed stream from the molecular sieve, contacting the molecular sieve with alkaline water under conditions effective to remove adsorbent poisons such as aromatic hydrocarbons from the molecular sieve, and removing water from the molecular sieve by contacting the molecular sieve with a vapor comprising a superheated $C_2$ to $C_9$ hydrocarbon. Preferably the adsorbent poisons are removed using liquid phase alkaline water containing sodium chloride.

DETAILED DESCRIPTION AND PREFERRED EMBODIMENTS

Olefinic hydrocarbons are very useful chemical compounds. They are reacted with themselves to form polymers or with other molecules in alkylation reactions in both the petrochemical and petroleum refining industries to make a wide variety of chemical products. It is often necessary for the olefins to be relatively high in purity in order to most effectively employ the olefins. At other times it is undesirable to have non olefinic hydrocarbons present in an olefin containing stream due to their formation of undesired by-products. In these instances it is necessary or at least desired to separate the olefins from nonolefinic hydrocarbons. In other instances the desired olefin is just one particular type of olefin such as a normal olefin or alpha olefin. which is a present in a mixture comprising other types of olefins such as iso olefins.

When a particular desired olefin is admixed with a chemical species of different relative volatility, the olefin is normally recovered from the admixture by fractional distillation. However, in many instances the olefin is present in a mixture containing one or more different hydrocarbons having rather similar volatilities, which make such a separation difficult or impossible. One common example of this is when the olefins are produced by the dehydrogenation of a paraffin or a mixture of paraffins. As the dehydrogenation reaction will not proceed to completion dues to equilibrium constraints, the product of the dehydrogenation zone is a mixture of paraffins and olefins of the same general chemical structure. These compounds will have very similar boiling points and are very difficult to separate by fractional distillation. In this instance adsorptive separation is often the most economical separation method, with the separation utilizing an adsorbent which is selective for one species; e.g., the olefins over the other.

The type of olefins recovered in the main olefin separation zone may be either straight chain or branched olefin depending on the application of the process. The nonrecovered hydrocarbons in the feed stream may be a different type of olefin. The process may therefore be specific to the recovery of normal olefin(s) from a mixture comprising isoolefins and/or paraffins. The olefinic product may comprise a single molecule such as isopentene or a mixture, such as of n-hexenes. The olefinic product may also comprise a several carbon number range of homologs such as the $C_{10}$ to $C_{14}$ linear olefins desired for use in the production of linear alkyl benzenes used as a detergent precursor.

The adsorptive separation can be performed using a variety of different techniques such as swing bed operation using two or more fixed beds with adsorption and regeneration steps cycling between them, moving bed operation in which the adsorbent is transported between adsorption and desorption zones and simulated moving bed (SMB) operation, such as described in U.S. Pat. Nos. 3,510,423; 3,720,604; 3,723,302 and 3,755,153. These patents are incorporated herein for their background teaching as to simulated moving bed adsorptive separation techniques and their description of adsorbents useful for adsorbent separations. Although simulated moving bed separations such as described in the above cited references are preferred, the manner in which the adsorbent is contacted with the olefin containing feed stream is not a limiting factor in the subject invention. The adsorbent regeneration procedure set out herein is applicable to any of these different adsorption techniques.

The separation process will basically comprise an adsorption step performed at adsorption conditions in which the adsorbent is brought into contact with the olefin containing feed and a desorption step in which selectively adsorbed olefins are removed from the adsorbent at desorption conditions. It is preferred that the desorption step is promoted through the contact of the adsorbent with a desorbent compound at conditions relatively similar to those employed in the adsorption step. However, the adsorbed olefins could be removed from the adsorbent by means of a change in temperature or pressure or both. That is, thermal swing adsorptive separation or pressure swing adsorptive separation could be used if desired. Pressure swing systems operate in vapor phase and the main olefin separation adsorption of the subject process may employ vapor phase adsorption and desorption conditions. These alternative desorption methods typically do not employ a desorbent.

The desorption step will produce a process stream containing a mixture of the desorbed olefins and any desorbent used in the process. This process stream is preferably passed into a desorbent separation and recovery zone which allows the desorbent to be recycled within the process.

The adsorbents employed in the subject process are preferably molecular sieves formed from inorganic oxides such as silica and alumina; that is, aluminosilicates. Such materials include the well know commercially available zeolites such as zeolite Y and zeolite X. The molecular sieve structure provided by many zeolites is important in the selectivity of the adsorbent for the olefinic hydrocarbon. However, it is believed the subject invention could also be employed to regenerate an inorganic oxide material which is not a zeolite but which is used as the adsorbent in a guard bed located upstream of the main olefin separation zone. The term molecular sieve is intended to include a broad variety of inorganic oxides which are suitable as guard bed adsorbents and/or as adsorbents for the separation of olefins including the silicalite materials described in the above cited references. Silicalites are very high silica to alumina ratio molecular sieves which are not zeolites due to their lack of ion exchange capacity. Silicalites are described in greater detail in U.S. Pat. Nos. 4,061,724; 4,073,865 and 4,104,294. Another type of inorganic oxide molecular sieve which could be used in the adsorbent is the ZSM type zeolite such as disclosed in U.S. Pat. No. 3,702,886 (ZSM-5), U.S. Pat. No. 3,832,449 (ZSM-12), U.S. Pat. No. 4,016,245 (ZSM-35) and U.S. Pat. No. 4,046,859 (ZSM-38).

The preferred adsorbent for use in the separation zone is an attrition resistant particle of about 20–40 mesh (U.S.) size formed by extrusion or spray drying an admixture of a binder such as clay or alumina and a type X or type Y zeolite. The type X zeolite is described in U.S. Pat. No. 2,822,244 and the type Y zeolite is described in U.S. Pat. No. 3,130,007. The zeolites may be ion exchanged to replace native sodium with one or more other cations selected from the alkali metals, the alkaline-earth metals and the coinage metals. Preferred metals include lithium, potassium, calcium, strontium and barium. Combinations of two or more of these metals may be employed. The preferred level of ion-exchange of these materials is rather low. One highly preferred adsorbent is a sodium form 13X zeolite. The same or a different molecular sieve can be used to adsorb the sieve poisons in the guard bed. The molecular sieve used in the guard bed is preferably highly exchanged with the desired cation.

An operational problem related to the adsorptive separation of olefins is the accumulation of certain compounds, present in the feed stream, on the active sites of the adsorbent. These compounds tend to bind so tightly to the sites that the desorption procedure used for olefin recovery does not remove them. They thus render these cites unusable for adsorption of the intended olefin. These compounds are often referred to as adsorbent poisons. As the deleterious effects grow due to the accumulation of more poison from the feed stream, the capacity of the adsorbent and thus the overall process is decreased. The composition of such poisons can vary, with the most common ones encountered in the subject process being diolefins and aromatic hydrocarbons. These include aromatic hydrocarbons containing a hetero atom such as sulfur or oxygen either in their ring structure or in alkyl side chains. Higher molecular weight aromatics are greater poisons. It is an objective of the subject invention to provide a means for removing adsorbent poisons from the adsorbents used in the separation of an olefin from another chemical compound. Specific examples of compounds which are considered as poisons in the preferred embodiment of the invention include benzene, toluene, other alkylated benzenes, butadiene, xylenes, ethylbenzene, tetralines, indanes, alkylated-dinaphthalenes, and bi phenyles. Other poisons include aniline, the cresols, pyridine, decaline and tetralin; oxygenates such as phenols, naphthenophenols, napthols, benzo furans and dibenzo furans; nitrogen compounds such as pyroles, pyridines, indoles naphthenopyridenes and carbazoles; and sulfur compounds such as benzothiophene, sulfolane, dimethyl benzothiophene, thiophene and benzenthiol.

It is a specific objective of the invention to provide a means for removing diolefins and/or aromatics from adsorbents comprising a molecular sieve. It is also an objective to provide such a method which is highly compatible with the preferred adsorbents used for the separation of linear olefins and the operation of a SMB process for olefin separation.

The art has recognized that it is desirable to prevent such poisons from deactivating the molecular sieves used to separate olefins as shown by the process described in the previously cited U.S. Pat. No. 5,300,715. In this process a selective aromatics removal zone is employed to prevent the entrance of aromatics into the adsorptive separation zone. It is stated in the patent that the aromatics removal zone can itself employ a regenerable adsorbent such as a molecular sieve. The reference also describes in general terms that the adsorbent of this zone can be regenerated as by use of liquid benzene. It is not desirable to use benzene as a regenerant in the subject process, especially in regenerating a guard bed, as small amounts of benzene will unavoidably remain in the system and migrate downstream to the main adsorptive separation zone causing deactivation of the sieves in this zone. The subject method of removing adsorbent poisons from molecular sieves can be applied to the sieves used in a guard bed upstream of the main olefin separation zone as well as for rejuvenation of the molecular sieves of the main olefin separation zone.

The subject rejuvenation procedure comprises first removing the olefin-containing feed stream from the molecular sieve. At this time the flow of the feed stream will be diverted to another quantity of molecular sieve or possibly stopped if the entire main adsorptive separation zone is being treated. The feed stream will normally be drained from the molecular sieve and if desired further flushed from the sieve by a relatively poison and olefin free hydrocarbon stream. If available, it is preferred to use a paraffin stream already found in the process. This is preferably performed at conditions similar to the normal operating conditions of the sieve being treated. This flush stream is then drained from the molecular sieve.

The poisons are then removed from the molecular sieve by contacting the sieve with liquid phase water at regeneration conditions. This contacting can be performed at a wide range of conditions which meet this criteria. It is preferred that the regeneration water has a temperature above about 100° F. (38° C.), with a broad range of operating temperatures for this procedure being from about 80 to about 250° F. (27–121° C.). A high temperature which might start to effect the structure or characteristic of the molecular sieve is to be avoided. It is important that the water has an alkaline pH, preferably above 8 and more preferably equal to 9 or higher.

The invention may therefore be summarized as a process for removing an adsorbent poison(s) from a molecular sieve used in a process for the separation of a first type of hydrocarbon from a mixture comprising said first type of hydrocarbon and a second type of hydrocarbon which comprises contacting the molecular sieve with alkaline liquid phase water under conditions effective to remove aromatic hydrocarbon originally present in the feed stream from the molecular sieve, and removing water from the molecular sieve by contacting the molecular sieve with a vapor comprising a superheated $C_2$ to $C_9$ paraffinic hydrocarbon The adsorbent is normally retained in the process in a fixed bed, and in-situ regeneration therefore requires passage of the regeneration fluids through the stationary bed of adsorbent. The amount of water which must be passed through the adsorbent can be determined by rather simple small scale tests. The use of the minimum required amount is preferred to avoid the production of large quantities of contaminated water. A slow rate of flow, e.g., 0.5 to 5.0 liquid hourly space velocity (L.H.S.V.) and a total quantity less than 4 times the volume of the adsorbent bed is therefore preferred.

It is important that the water contains a cation to maintain the pre-existing cation within the molecular sieve and to prevent ion exchanging the molecular sieve to the hydrogen form. In a preferred embodiment of the invention the water contains a lithium and/or chloride ion to prevent loss of the respective cation(s) from the preferred molecular sieves. The preferred means of providing the especially desired chloride ion content is by the use of a sodium chloride solution. Water containing from about 0.5 to about 2.5 wt. % sodium chloride is preferred. In embodiments in which the molecular sieve contains a different ion(s) the content of the water should be adjusted accordingly. In some instances however it will not be necessary or desired for the water to contain any specific ion. One example of this is the regeneration of a cation-free molecular sieve.

Following the removal of adsorbed poisons by the water, the adsorbent is "dried" preferably by contact with vaporized poison-free hydrocarbons. While contact with liquid phase hydrocarbons could be used, vapor-phase hydrocarbons bring in more heat to drive off water. The term dried is relative as it is only desired to remove enough water to return the adsorbent to the degree of hydration at which it is normally used in the adsorptive separation. As known to those skilled in the art of adsorptive separation, the degree of hydration is often very important to the capacity and/or selectivity of an inorganic molecular sieve. In the case of the preferred adsorbent the preferred range of hydration is from about 1.0 to 3.0 wt percent. The hydrocarbon used to dry the adsorbent can be any relatively light hydrocarbon which does not adversely affect the sieve. Preferably the drying hydrocarbon comprises a light paraffin having from 3 to 10 carbon atoms per molecule such as pentane or normal heptane. The use of a hydrocarbon already available in the process is preferred as this has a definite economic benefit. It is therefore preferred to employ a material such as the desorbent material in the drying procedure. The desorbent stream is often a mixture of two or more different hydrocarbons, and the hydrocarbon stream employed to dry the adsorbent may therefore also contain a mixture of light hydrocarbons. A common mixture would be a paraffin and olefin of the same molecular weight and structure. For instance a mixture of hexene and hexane can be employed. It is also possible to employ a mixture where the paraffin and olefin have different carbon numbers such as a mixture of n-heptane and n-octenes. After the adsorbent is dried in this manner it is returned to its operational temperature and is ready to employ in the separation process. This drying step may be performed at a pressure from atmospheric to about 200 psig (1380 kPa) or more and at a temperature of about 20 to about 250° C.

The following is an example of the invention based upon the regeneration of a quantity of the preferred 13X zeolite-containing adsorbent. During commercial operation the desorbent had lost a significant amount (over 40%) of its adsorptive capacity due to the accumulation of one and two ring aromatics (some of which contained S, N and O). The adsorbent was contacted with one bed volume of a 1.5 wt % aqueous sodium chloride solution having a pH of 8 for 15 minutes at a L.H.S.V. of $4.0^{hr-1}$ and a temperature of 40° C. The adsorbent was then dried to the target moisture content (1–3%) using normal pentane vapor having a temperature of about 175° C. After this the adsorbent was found to have an adsorptive capacity equal to its fresh (unused) state.

A preferred embodiment may be therefore characterized as a process for the separation of linear olefinic hydrocarbons from a feed stream comprising linear olefinic hydrocarbons and other types of hydrocarbons, which process comprises contacting the feed stream with a bed of a molecular sieve under conditions which cause the selective retention of olefinic hydrocarbons on the molecular sieve and recovering the olefinic hydrocarbons by contacting the molecular sieve with a desorbent, and periodically regenerating a molecular sieve used in the process by purging the feed stream from the molecular sieve, contacting the molecular sieve with alkaline liquid phase water under conditions effective to remove aromatic hydrocarbons originally present in the feed stream from the molecular sieve, and removing water from the molecular sieve by contacting the molecular sieve with a vapor comprising a superheated $C_2$ to $C_9$ paraffinic hydrocarbon.

What is claimed:

1. A process for the separation of a first type of hydrocarbons from a feed stream comprising said first type of hydrocarbons and at least one other type of hydrocarbon, which process comprises periodically regenerating a molecular sieve used in the process by purging the feed stream from the molecular sieve, contacting the molecular sieve with alkaline water under conditions effective to remove adsorbent poisons from the molecular sieve, and removing water from the molecular sieve by contacting the molecular sieve with a vapor comprising a superheated $C_2$ to $C_9$ hydrocarbon.

2. The process of claim 1 wherein the molecular sieve is an aluminosilicate.

3. The process of claim 1 wherein the water is present as a liquid having a pH above 8.

4. The process of claim 3 wherein the molecular sieve is a silicalite.

5. The process of claim 3 wherein the molecular sieve is a ZSM zeolite.

6. The process of claim 1 wherein the molecular sieve is a type X zeolite.

7. The process of claim 1 wherein the water contains sodium ions.

8. A process for removing an adsorbent poison from a molecular sieve used in a process for the separation of a first type of hydrocarbon from a mixture comprising said first type of hydrocarbon and a second type of hydrocarbon which comprises contacting the molecular sieve with alkaline liquid phase water under conditions effective to remove an aromatic hydrocarbon originally present in the feed stream from the molecular sieve, and removing water from the molecular sieve by contacting the molecular sieve with a vapor comprising a superheated $C_2$ to $C_9$ paraffinic hydrocarbon.

9. A process for the separation of linear olefinic hydrocarbons from a feed stream comprising linear olefinic hydrocarbons and other types of hydrocarbons, which process comprises contacting the feed stream with a bed of a molecular sieve under conditions which cause the selective retention of olefinic hydrocarbons on the molecular sieve and recovering the olefinic hydrocarbons by contacting the molecular sieve with a desorbent, and periodically regenerating a molecular sieve used in the process by purging the feed stream from the molecular sieve, contacting the molecular sieve with alkaline liquid phase water under conditions effective to remove aromatic hydrocarbons originally present in the feed stream from the molecular sieve, and removing water from the molecular sieve by contacting the molecular sieve with a vapor comprising a superheated $C_2$ to $C_9$ paraffinic hydrocarbon.

10. The process of claim 9 wherein the water is present as a liquid having a pH above 8.

11. The process of claim 9 wherein the molecular sieve is a ZSM zeolite.

12. The process of claim 9 wherein the molecular sieve is an aluminosilicate.

13. The process of claim 9 wherein the molecular sieve is an X zeolite.

14. The process of claim 9 wherein the water contains lithium and/or sodium ions.

15. The process of claim 9 wherein the molecular sieve which is regenerated is contained in a guard bed upstream of a main bed of molecular sieve used to separate the olefinic hydrocarbons.

* * * * *